US008173405B2

(12) United States Patent
McNeil et al.

(10) Patent No.: US 8,173,405 B2
(45) Date of Patent: May 8, 2012

(54) NEROLIDOL, TERPENE, AND TERPENE DERIVIATIVE SYNTHESIS

(75) Inventors: Caroline Virginia McNeil, Houston, TX (US); Pietro Morlacchi, Houston, TX (US); Alyssa Baevich, Richmond, TX (US); Seiichi Paul Tillich Matsuda, Houston, TX (US)

(73) Assignee: William Marsh Rice University, Houston, TX (US)

( * ) Notice: Subject to any disclaimer, the term of this patent is extended or adjusted under 35 U.S.C. 154(b) by 340 days.

(21) Appl. No.: 12/516,164

(22) PCT Filed: Dec. 12, 2007

(86) PCT No.: PCT/US2007/087254
§ 371 (c)(1),
(2), (4) Date: May 22, 2009

(87) PCT Pub. No.: WO2008/076758
PCT Pub. Date: Jun. 26, 2008

(65) Prior Publication Data
US 2010/0062504 A1    Mar. 11, 2010

Related U.S. Application Data

(60) Provisional application No. 60/869,854, filed on Dec. 13, 2006.

(51) Int. Cl.
*C12P 7/04*    (2006.01)
(52) U.S. Cl. .................. 435/157; 435/171; 435/254.11; 435/254.2; 435/254.21

(58) Field of Classification Search ...................... None
See application file for complete search history.

(56) References Cited

U.S. PATENT DOCUMENTS

2003/0096385 A1   5/2003   Muramatsu et al.
2004/0072323 A1*  4/2004   Matsuda et al. ........... 435/252.3

OTHER PUBLICATIONS

International Preliminary Report on Patentability; PCT/US2007/087254; pp. 5, Jun. 25, 2009.
International Search Report and Written Opinion; PCT/US07/87254; pp. 6, Oct. 21, 2008.
Bergstrom et al.; "Zaragozic Acids: A Family of Fungal Mteabolites That are Picomolar Competitive Inhibitors of Squalene Synthase"; Proc. Natl. Acad. Sci., vol. 90; pp. 80-84, 1993.
Zhang et al.; "Genomic Scale Mutant Hunt Identifies Cell Size Homeostasis Genes in *S. cerevisiae*"; Current Biology, vol. 12; pp. 1992-2001, 2002.
Panaretou et al.; "ATP Binding and Hydrolysis are Essential to the Function of the Hsp90 Molecular Chaperone in Vivo"; The EMBO Journal, vol. 17, No. 16; pp. 4829-4836, 1998.

* cited by examiner

*Primary Examiner* — Susan Hoffman
(74) *Attorney, Agent, or Firm* — Baker Botts L.L.P.

(57) ABSTRACT

According to one embodiment, the description relates to a method of nerolidol production. The method includes culturing a yeast strain lacking functional squalene synthase and overproducing HMG CoA reductase in synthetic medium lacking uracil and producing nerolidol. The pH of the medium may be adjusted to an acidic level to further increase nerolidol production. Other chemicals may also be produced by this method. The nerolidol or other chemicals may be removed from the yeast or medium or both. The medium may additionally contain a polyaromatic resin, which may adsorb nerolidol or other chemicals.

19 Claims, 1 Drawing Sheet

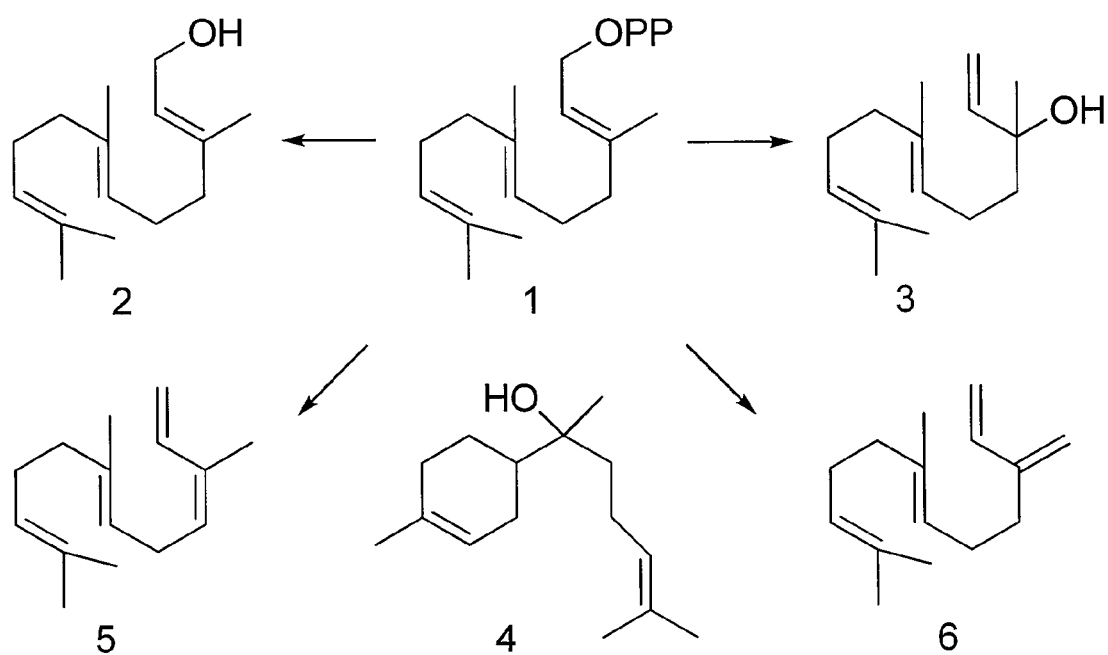

NEROLIDOL, TERPENE, AND TERPENE DERIVIATIVE SYNTHESIS

PRIORITY CLAIM

The present application claims priority to previously filed U.S. Provisional Patent Application Ser. No. 60/869,854, filed Dec. 13, 2006 and titled "Nerolidol, Terpene and Terpene Derivative Synthesis."

TECHNICAL FIELD

The present invention relates to nerolidol synthesis and the synthesis other molecules and derivatives thereof. In particular embodiment, it relates to a method of increasing nerolidol or other chemical synthesis in yeast through the use of a particular culture medium, such as a synthetic medium lacking uracil, an also to a method of increasing nerolidol or farnesol synthesis by controlling the pH of the culture medium.

TECHNICAL BACKGROUND

Sesquiterpenoids are which is a terpenes having three isoprene units ($C_{15}$ compounds). Seqsquiterpenoids are a large class of natural products isolated mainly from plants and responsible for a wide variety of natural fragrances and flavors. Among these are the linear sesquiterpene alcohols nerolidol and farnesol, which have applications in plant defense, flavor and fragrance and medicine. Nerolidol, for example, is used to enhance transdermal drug delivery.

Nerolidol is derived from farnesyl pyrophosphate (FPP) (also called farnesyl diphosphate) through a substitution reaction. Most eukaryotes synthesize farnesyl pyrophosphate as a sterol precursor. Nerolidol is currently obtained through chemical synthesis or by isolation from a natural source. Both of these methods are expensive and produce low yields. Thus, a need exists from a method of nerolidol production that is either cheaper, has a higher yield, or provides other advantages.

SUMMARY

According to one embodiment, the invention relates to a method of nerolidol production. The method of producing nerolidol includes culturing a yeast strain lacking functional squalene synthase and overproducing HMG CoA reductase in synthetic medium lacking uracil. Other chemicals may also be produced by this method. The nerolidol or other chemicals may be removed from the yeast or medium or both. The medium may include individual amino acids, nucleotides, minerals, and a carbon source. The medium may additionally contain a polyaromatic resin, which may adsorb nerolidol or other chemicals.

According to another embodiment, nerolidol or farnesol may be produced by controlling pH of the culture medium, with a more acidic pH resulting in increased nerolidol production.

For a more complete understanding of the present disclosure and the advantages thereof, reference is now made to the following drawings and description.

BRIEF DESCRIPTION OF THE DRAWINGS

Aspects of the present invention maybe better understood through reference to the following drawings.

FIG. 1 shows farnesyl pyrophosphate (1) hydrolysis in yeast to farnesol (2), nerolidol (3), geranyl pyrophosphate (4), α-farnesense (5) and β-farnesene (6), which hydrolysis may be controlled according to embodiments of the present invention.

DETAILED DESCRIPTION

The current invention relates to nerolidol synthesis and the synthesis of similar molecules and their derivatives. Yeast normally produce farnesyl pyrophosphate (FPP), which is the precursor to squalene in the sterol biosynthetic pathway. However an absence of functional squalene synthase prevents the conversion of farnesyl pyrophosphate to squalene, and it therefore causes farnesyl pyrophosphate to accumulate. However, farnesyl pyrophosphate is not very stable and tends to be hydrolyzed to other compounds, many of which are shown in FIG. 1. Farnesyl pyrophosphate is typically hydrolyzed to primarily to farnesol and only trace amounts of nerolidol are formed. Embodiments of the current invention are derived from the discovery that, when grown in certain media, yeast will produce increased amounts of nerolidol. Control of pH may also increase production of nerolidol.

In one embodiment, the invention includes a method for producing nerolidol from yeast by growing the yeast in a synthetic complete medium or other medium lacking uracil. In some embodiments using this method, nearly all of the farnesyl pyrophosphate in the yeast may be hydrolyzed to nerolidol. Further shifts to production of nerolidol as opposed to farnesol may be accomplished by adjusting the pH of the medium to be more acidic either initially, at the end of the growth cycle, or during the growth cycle.

Methods of the current invention may be carried out in yeast. Standard methods and reagents in the field of yeast molecular genetics, particularly regarding *Saccharomyces cerevisiae*, are well known in the art. References for such methods include *Methods in Yeast Genetics*, 2000 *Edition: A Cold Spring Harbor Laboratory Course Manual* (Burke et al., 2000) and *Current Protocols in Molecular Biology*, Chapter 13 (Ausubel et al., 1994), both incorporated by reference herein. A skilled artisan is aware that *Saccharomyces* is a yeast of choice, which includes many known species such as *S. cerevisiae, S. italicus, S. oviformis, S. capensis, S. chevalieri, S. douglasii, S. paradoxus, S. cariocanus, S. kudriavzevii, S. mikatae, S. bayanus* and *S. pastorianus. S. Cerevisiae*, for example, is a good choice because it naturally produces farnesyl pyrophosphate. Other microorganisms with this ability may similarly provide good choices for use in embodiments of the current invention.

The yeast may be modified to regulate its metabolism, particularly aspects of its metabolism that may influence nerolidol synthesis. Some such modified yeast, methods of modification and effects of modification are described in U.S. patent application Ser. No. 10/041,018, which is incorporated by reference herein. In a particular embodiment, the yeast may be modified to not produce effective squalene synthase. For example it may have a deletion of its squalene synthase gene or a modification that only allows it to produce nonfunctional squalene synthase.

Squalene synthase is typically produced by erg9 in yeast. In a specific embodiment, at least one ERG9 (squalene synthase) (GenBank Accession No. X59959) modification is generated by standard means in the art to create a "bottleneck" in the farnesyl pyrophosphate pathway, thereby providing increased amounts of farnesyl pyrophosphate for transformation into nerolidol. One way to partially block squalene synthase activity may achieved by employing a temperature-sensitive mutation which allows examination of impaired enzymatic activity without the adverse effect of completely blocking metabolism. Temperature-sensitive mutations weaken an enzyme's secondary structure. The resultant protein becomes especially sensitive to thermal denaturation, thereby rendering its activity temperature-sensitive. A temperature-sensitive ERG9 mutation (Karst et al., 1971) is known. A yeast strain comprising the erg9-1 temperature-sensitive mutation may be purchased from American Type Culture Collection (ATCC 64031).

The yeast may also be modified to overexpress HMG CoA reductase, causing an increase in throughput to farnesyl pyrophosphate. Overexpression of HMG CoA reductase may be achieved by many methods. In one embodiment, a truncated HMG1 (3-hydroxy-3methylglutaryl CoA reductase) may be expressed using an inducable promoter such as GALL HMG CoA reductase may also be truncated in other manners.

HMG CoA reductase is a rate-limiting enzyme in early sterol biosynthesis in eukaryotic cells. Yeast have two isozymes of HMG CoA reductase, Hmg1p and Hmg2p, produced from genes on separate chromosomes (Basson et al., 1986), although the vast majority of reductase activity under normal conditions is the result of Hmg1p activity. Null mutations in both genes cause lethality, yet null mutations in either gene alone are viable although survival is reduced (Basson et al., 1987).

A skilled artisan is aware that increasing significant levels of HMG CoA reductase in a yeast cell, which is membrane-bound in most organisms, results in generation of extensive membrane structures (Profant et al., 1999) that is detrimental to diterpene and diterpene precursor biosyntheses and possibly also detrimental to nerolidol synthesis. It is also well known that there are two native S. cerevisiae HMG CoA reductases, both of which have a N-terminus transmembrane spanning domain (1.6 kb).

In a specific embodiment of the present invention, endogenous copies of both HMG1 and HMG2 remain intact in the yeast which harbors the recombinant nucleic acid sequence encoding a soluble form of HMG CoA reductase. Alternatively, the endogenous copies of HMG1 and HMG2 may be wholly or partially disrupted to prevent or decrease the production of the membrane-bound form of HMG CoA reductase.

Soluble HMG CoA reductase may be produced from versions of HMG1, HMG2, other genes encoding HMG CoA reductase, and variants thereof which lack sequences responsible or associated with transmembrane domains. These structures are easily identified by standard means in the art, such as commercially available computer programs including Genetics Computer Group® (Madison, Wis.). For example, to eliminate the rate limitation associated with this enzyme in the yeast Saccharomyces cerevisiae, a truncated HMG1 gene producing a form of the enzyme that lacks the membrane-binding region (i.e. amino acids 1-552) (Polakowski et al., 1998) may be used.

Examples of HMG CoA reductase nucleic acid sequences, which in specific embodiments may be altered to achieve solubility of the reductase, include the Saccharomyces cerevisiae open reading frame found on chromosome XIII at locus YML075C; NM 000859; X00494; AF273765; AF273764; AF273763; AF273762; AF273761; AF273760; AF273759; AF273758; AF273757; AF273756; AF273755; AF273754; AF290098; AF290096; AF290090; AF290088; AF290086; AF071750; AB037907; AF155593; X58370; AF162705; AF159136; AF159138; AB015627; AB015626; AV374599; AV317420; AV317328; AV317132; AV277976; AV259312; AV237573; AF142473; E17178; E17177; AF110382; AB021862; U97683; A1326595; U33178; U30179; L34829; L34824; AB012603; AA982887; AF038045; AA710790; AA597171; AA517939; U51986; U51985; AA260731; AA109510; L76979; X70034; X94308; X68651; X94307; A10474; A10471; A10468; A10465; A10462; X55286; J04537; A10473; A10470; A10467; M15959; M62633; M62766; M12705; M22002; L19261; J04200; J03523; M27294; M24015; or a combination thereof.

Examples of HMG CoA reductase amino acid sequences that may be subsequently altered to achieve solubility of the reductase for the present invention include the following: NP_013636.1; NP_000850.1; CAA25189.1; AAG02454.1; AAG02449.1; AAG02434.1; AAG02429; AAG02423.1; AAD20975.2; BAB07821.1; AAD38406.1; CAA41261.1; AAF80475.1; AAF80374.1; BAA74566.1; BAA74565; AAD47596.1; AAD38873.1; BAA36291.1; AAD09278; AAC46885.1; AAC37437.1; AAC37436.1; AAC37435.1; AAC37434.1; AAC37433.1; AAC37432.1; AAC37431.1; BAA31937.1; AAC05089.1; AAC05088.1; AAB67527.1; BAA06492.1; AAB52552.1; AAB52551.1; AAB39277.1; CAA49628.1; CAA63971.1; CAA48610.1; CAA63970.1; CAA39001.1; AAA76821.1; CAA00908.1; CAA00907.1; CAA00906.1; CAA00905.1; CAA00904.1; AAA67317.1; AAA37819.1; AAA37077.1; AAA34677.1; AAA32814.1; AAA30060.1; AAA29896.1; AAA25894.1; AAA25837.1; P43256; A23586; 512554; 572194; T07112; S56715; 556714; 556712; 556711; S56710; 533175; 028538; AAA25837; 026662; Q58116; Q59468; P54960; P48019; P48020; Q01559; Q03163); Q00583; P13702; P14891; Q9YAS4; Q9Y7D2; Q9XHL5; Q9XEL8; Q9V1R3; Q9V1R3; Q41437; 076819; 074164; 064967; 064966; 059469; 051628; 024594; NP_000850; CAA25189; NP_013555; NP_013308; AAA36989; Q12649; P04035; AAG21343; AAG02454; AAG02449; AAG02434; AAG02429; AAG02423; AAD20975; BAB07821; AAD38406; AAF80475; AAF80374; AAF80373; Q12577; BAA74566; BAA74565; P54869; 002734; 008424; Q10283; Q29512; P51639; P54839; P54874; Q01581; P54872; P54871; P54873; P54868; P54870; P54961; P48021; P48022; P34136; P34135; Q01237; P20715; P16237; P09610; P14773; P00347; P12684; P29058; P12683; P29057; P17425; P13704; P23228; P22791; AAD47596; 5542336; 5542335; 5542334; 5542333; AAD38873; BAA36291; AAD09278; AAC46885; AAC37437; AAC37435; AAC37434; AAC37433; AAC37432; AAC37431; AAC37436; BAA31937; AAC05089; AAC05088; AAB67527; AAB52552; AAB52551; AAB39277; CAA49628; 2116416F; 2116416E; 2116416D; 2116416C; 2116416B; 2116416A; CAA63971; CAA63970; CAA39001; CAA00906; CAA00907; CAA00908; CAA00904; AAA67317; AAA37819; AAA37077; AAA32814; AAA29896; RDHYE; and AAA25894.

One yeast strain lacking functional squalene synthase to do an ERG9 deletion and overproducing HMG CoA reductase via addition of truncated HMG1 has been designated PMY1.

When yeast strains, including those lacking functional squalene synthase and overproducing HMG CoA reductase, are grown in conventional media (e.g. broths made of biological sources such as yeast extract and peptone, i.e. hydrolyzed meat protein), with a carbon source, farnesyl pyrophosphate is converted to farnesyl, which then accumulates. The mechanism of this transformation is unknown, but likely is catalyzed by a yeast enzyme or occurs through non-enzymatic hydrolysis.

Two yeast phosphatases, DPP1 and LPP1 have previously been shown to hydrolyze farnesyl pyrophosphate and other prenyl pyrophosphates. Therefore, deletion of these genes in yeast may be expected to reduce expression of farnesyl pyrophosphate hydrolysis products in yeast. However, experiments have shown this not to be the case. Accordingly, the hydrolysis of farnesyl pyrophosphate to nerolidol or farnesol described herein is likely not controlled by DPP1 or LPP1.

When yeast lacking a functional squalene synthase and overproducing HMG CoA reductase are grown in synthetic medium, in some embodiments a synthetic complete medium, lacking uracil, the farnesyl pyrophosphate is hydrolyzed largely to nerolidol (3) instead of farnesyl (2). In a particular embodiment, the medium lacks uracil, but contains individual amino acids, nucleotides, minerals and a carbon source.

According to a specific embodiment, the medium may contain:
1) Amino acids—alanine, arginine, aspartic acid, asparagine, cysteine, glutamic acid, glutamine, glycine, histidine, isoleucine, leucine, lysine, methionine, phenylalanine, proline, serine, threonine, tryptophan, tyrosine and valine (e.g. all 20 amino acids)
2) Adenine
3) Yeast nitrogen base (1.7 g/L) with:
   Biotin 2 µg
   Calcium pantothenate (or D-pantothenic acid) 400 µg
   Folic acid 2 µg
   Inositol 2000 µg
   Niacin 400 µg
   p-Aminobenzoic acid 200 µg
   Pyridoxine hydrochloride 400 µg
   Riboflavin 200 µg
   Thiamine hydrochloride 400 µg
   Boric acid 500 µg
   Copper sulfate 40 µg
   Potassium iodide 100 µg
   Ferric chloride 200 µg
   Manganese sulfate 400 µg
   Sodium molybdate 200 µg
   Zinc sulfate 400 µg
   Potassium phosphate monobasic 1 g
   Magnesium sulfate 500 mg
   Sodium chloride 100 mg
   Calcium chloride 100 mg
4) Ammonium sulfate (5 g/liter)

Sugar solutions of dextrose or galactose may be used as carbon sources.

In one example, *S. Cervisiae* modified to delete erg9 and to contain a truncated HMG1 (3-hydroxy-3methylglutaryl CoA reductase) expressed using an inducible GAL1 promoter was grown in the medium described above. Approximately 50 mg/L of nerolidol was produced by these yeast.

Accordingly, one embodiment of the invention includes a method of producing nerolidol by culturing a yeast strain lacking functional squalene synthase and overproducing HMG CoA reductase in synthetic medium lacking uracil to produce at least approximately 50 mg/L of nerolidol. This nerolidol may then be removed from the medium, the yeast or, more commonly, both.

pH of culture medium also influences nerolidol sythesis in a yeast strain lacking functional squalene synthase and overproducing HMG CoA reductase. In particular, a more acidic media pH causes increased production of nerolidol, while a more basic pH causes increased production of farnesol. For example, when the PMY1 yeast strain is grown through saturation phase grown in rich (YP) media versus minimal (SC-U) media, or combinations of these media, significant differences are seen in production of farnesol (2) versus nerolidol (3). YP is more basic than SC-U. Results of one such experiment are shown in Table 1 and indicate that use of more basic media causes production of farnesol, whereas use of more acidic media causes production of nerolidol.

TABLE 1

Growth of PMY1 in YP or SC-U

| Media | Farnesol (mg/L) | Nerolidol (mg/L) | Initial pH | Final pH |
| --- | --- | --- | --- | --- |
| YP | 25.17 +/− 6.807 | 3.103 +/− 0.0611 | 6.5-7 | 5.5 |
| SC-U* | 8.920 +/− 1.860 | 19.47 +/− 2.977 | 5.5 | 4-4.5 |
| SC-U/YP (1:1)* | 14.92 +/− 1.762 | 2.113 +/− 0.1935 | 6.1 | 5.0 |

*PMY1 grown in SC-U containing media additional contained the common yeast plasmid pRS316Gal.

In separate experiments, when the initial pH of YP was adjusted to be acidic (5-5.5) and the initial pH of SC-U was adjusted to be basic (7-7.5), nerolidol production in YP was significant whereas farnesol production in SC-U was significant, indicating that media pH is the controlling factor.

Accordingly, yeast lacking functional squalense synthase and overexpressing HMG CoA reductase may be grown in medium either naturally having an acidic pH or adjusted to have an acidic pH in order to increase nerolidol production. In specific embodiments, the medium may have an initial pH of 6.0 or less, 5.5 or less, or 5.0 or less. Conditions may also be adjusted to control pH during growth to be more acidic. In specific embodiments, after reaching saturation phase growth, the medium may have a pH of less than 5.0, 4.5 or less or 4.0 or less.

The amount of nerolidol produced may vary depending on the yeast strain, its modifications, presence or absence of polyaromatic resin in the medium, culture conditions, length of culture, and other factors.

According to one theory, to which the current invention is not restricted, the medium may cause non-enzymatic hydrolysis of farnesyl phosphate to nerolidol. This theory is supported by the presence of a racemic mixture of nerolidol in cultures of PMY1 yeast in medium lacking uracil and having an acidic pH. If hydrolysis were enzymatic, single enantiomers of nerolidol would typically be expected.

A polyaromatic resin may be added to the medium to adsorb excreted nerolidol. This may increase nerolidol production in the yeast. In one embodiment, the medium may be supplemented with 5% (w/v) sterile polyaromatic resin.

Other valuable chemicals may also be extracted from the medium in addition to or in place of nerolidol. For example, yeast grown according to the methods described above may also produce relatively high amounts of the sesquiterpene alcohol, farnesol. Addition of a prenyl alcohol transferase to the yeast may lead to the production of linear monoterpene or diterpene alcohols, such as linalool or gernaylgeraniol. Further modifications to the yeast may produce squalene, sesquiterpenoids, or vitamin precursors.

Purification of the products of PMY1 grown in medium lacking uracil and having an acidic pH, followed by chromatographic purification and analysis by GC-MS and NMR spectra reveals that various additional sesquiterpene compounds are present. Products found are shown in FIG. 1 and included geranyl pyrophosphate (4), α-farnesene (5), and β-farnesene (6).

While the compositions and methods of this disclosure have been described in terms of specific embodiments, it will be apparent to those of skill in the art that variations may be applied to the compositions and/or methods and in the steps or in the sequence of steps of the methods described herein without departing from the concept, spirit and scope of the invention. For example, although the current description focuses on production of nerolidol, the disclosure may also be used by one of ordinary skill in the art to increase yields of farnesol or other hydrolysis products of farnesyl pyrophosphate. All such similar substitutes and modifications apparent to those skilled in the art are deemed to be within the spirit, scope and concept of the invention.

The invention claimed is:

1. A method of nerolidol production comprising:
 culturing a yeast strain lacking functional squalene synthase and overproducing HMG CoA reductase in synthetic medium lacking uracil; and
 producing nerolidol in a concentration of at least approximately 50 mg/L.

2. The method according to claim 1, further comprising removing the nerolidol from the yeast or medium, or both.

3. The method according to claim 1, wherein the yeast strain is a modified *S. Cerevisiae* yeast strain.

4. The method according to claim 1, wherein the yeast strain has a deletion of erg9 and expresses a truncated HMG1.

5. The method according to claim 1, wherein the medium comprises a polyaromatic resin.

6. The method according to claim 5, wherein the medium comprises the polyaromatic resin in concentration of 5% (w/v).

7. The method according to claim 1, further comprising producing a sesquiterpene alcohol.

8. The method according to claim 1, further comprising producing a linear monoterpene or diterpene alcohol.

9. The method according to claim 1, further comprising producing a vitamin precursor.

10. The method according to claim 1, wherein the medium has pH of approximately 6.0 or less.

11. The method according to claim 10, further comprising producing farnesol.

12. The method according to claim 10, wherein the medium has an initial pH of approximately 6.0 or less.

13. The method according to claim 10, wherein the medium has an initial pH of approximately 5.5 or less.

14. The method according to claim 10, wherein the medium has an initial pH of approximately 5.0 or less.

15. The method according to claim 10, wherein culturing lasts until the yeast reach saturation phase growth, and wherein the medium has a pH of approximately 5.0 or less when the yeast reach saturation phase growth.

16. The method according to claim 10, wherein culturing lasts until the yeast reach saturation phase growth, and wherein the medium has a pH of approximately 4.5 or less when the yeast reach saturation phase growth.

17. The method according to claim 10, wherein culturing lasts until the yeast reach saturation phase growth, and wherein the medium has a pH of approximately 4.0 or less when the yeast reach saturation phase growth.

18. The method according to claim 10, further comprising adjusting the pH of the medium to approximately 6.0 or less.

19. The method according to claim 10, wherein the medium comprises synthetic complete medium lacking uracil.

* * * * *